United States Patent [19]
Goodfield

[11] 3,991,744
[45] Nov. 16, 1976

[54] PROCESS FOR TREATING PSYCHOPHYSIOLOGICAL CONDITION

[76] Inventor: Barry A. Goodfield, 3 Circle Drive, Ross, Calif. 94957

[22] Filed: Apr. 22, 1975

[21] Appl. No.: 570,403

[52] U.S. Cl. .................................. 128/2 H; 128/1 R
[51] Int. Cl.² ............................................ A61B 5/00
[58] Field of Search ..................... 128/1 R, 2 A, 2 H

[56] References Cited
UNITED STATES PATENTS
3,908,634   9/1975   Monaghan ........................... 128/1 R

*Primary Examiner*—Anton O. Oechsle
*Attorney, Agent, or Firm*—Warren, Chickering & Grunewald

[57] ABSTRACT

There is disclosed a process for treating a psychophysiologic condition which includes scanning all or part of the body of a human subject with a thermographic device which produces a visual display to determine areas of the subject's body exhibiting temperature aberrations, then inducing a hypnotic state in the subject while focusing the subject's attention on the area of the body exhibiting the temperature aberration, then regressing the subject to a traumatic experience affecting the part of the body exhibiting the temperature aberration and maintaining his attention focused on the traumatizing experience until the temperature aberration becomes unstable, after which the subject is brought out of the hypnotic state.

3 Claims, No Drawings

PROCESS FOR TREATING PSYCHOPHYSIOLOGICAL CONDITION

BACKGROUND OF THE INVENTION

Many people suffer from conditions that are described as psychophysiologic conditions. These conditions might be simply annoying, such as a lump in the throat, trembling hands, or profuse sweating. The conditions may also be debilitating to some degree, such as stiff muscles, sore back, or migraine headaches. More serious conditions might require treatment and therapy to maintain the person suffering from them functional.

Psychiatric treatment of such conditions is well known. Psychiatric treatment is usually required over an extended period of time, and it is very expensive. In psychiatric treatment a therapist helps the patient isolate the psychological basis for the problem and then facilitates the patient's insight to bring it into the patient's conscious awareness in such a manner that it can be dealt with successfully by the patient.

Usually it is difficult to isolate the psychological basis for a physiological condition. In all instances it requires prolonged discussion with the patient, and in many instances it is not within the patient's awareness at all. For example, a traumatizing experience could occur at a time in a patient's life that is earlier than he can remember — such as when he is an infant of one year old. As another example, a traumatizing experience could affect a different part of the body than the one having the psychophysiological condition. An example of this might be a frightening experience of a patient when his hand was caught or restrained by another person, by an animal, or by a device. In freeing his hand in a frightening emergency, he would pull the hand abruptly away to effect its release, and this experience could be "remembered" by the back or shoulder muscles which were exerted strenuously to effect such a release of the caught hand. Such a traumatizing experience would be an experience associated primarily with the hand, but the physiologic condition that it causes could be a sore back or a chronic headache caused by tense back muscles restricting blood flow which would be causally associated with the traumatizing experience but affecting a different part of the body. This is particularly true if the experience were one from early childhood and the memory of it were repressed.

It is postulated that the body remembers traumatizing experiences by various means. For example, a traumatic experience involving a back muscle may be remembered by that back muscle remaining in an unnatural state of tension to be ready for another similar emergency, and the resultant tension may so restrict the flow of blood that the muscle involved, or even another part of the body, is affected by the diminished blood flow through the tense muscle. These "memories" cannot be dealt with by the patient unless they are brought to his conscious awareness. Thus, if the patient is aware that his back muscle is tense because of an old traumatic experience, he can deal with these alert defenses by consciously relaxing them which can be done effectively when the destructive consequences of the alertness are in the patient's conscious awareness.

THE INVENTION

This invention is a process for quickly and effectively treating psychophysiologic conditions. The process of the invention includes scanning all or part of a human subject with a thermographic device that has a visual display of temperature variations over all or a selected area of the body of the subject. Employing the thermographic device, areas having temperature aberrations are isolated. After the areas with temperature aberrations have been isolated, the subject is placed in an hypnotic state, and while in that hypnotic state, the subject's attention is focused on the part of the body displaying the temperature aberration. While the subject's attention is so focused, the subject is regressed to a traumatizing experience affecting the area exhibiting the temperature aberration. When the subject in an hypnotic state is reexperiencing the traumatizing experience, the temperature aberration becomes unstable. The subject is maintained in an hypnotic state and reexperiences his traumatizing experience until the temperature aberration restabilizes, after which the subject is brought out of his hypnotic state.

The process described hereinabove can generally be effected within an hour, and it has produced dramatic results. In effect, an objective measurement is employed to isolate an area of the human body that has been psychologically traumatized, and known hypnotic techniques are employed to quickly regress the subject to that traumatizing experience and bring it into his conscious awareness where it can be dealt with. In addition, when the subject observes the visual display during his regression, he can observe an objective measurement of the feelings he is experiencing and with the aid of such "feedback" can progress to the point where the subconscious traumatizing experience is brought to his conscious awareness at a much faster rate.

The first stage of the process of this invention is scanning a human subject with a thermographic means having a visual display of temperature variations. The scan preferably is preceded by an interview of the subject to determine which portion of his body is affected with the physiologic condition. In that manner, the scan may be isolated to limited areas of the body with greater resolution from the equipment that is employed. The temperature scan is preceded with a period wherein the patient comes to thermal equilibrium. This is generally accomplished by the subject baring those parts of his body to be scanned for sufficient time for the parts to come to equilibrium with the surrounding temperature, which is maintained constant. The subject may be scanned several times to see if the temperature of his body surfaces is changing and to establish a norm for that particular subject — i.e., to establish his normal body surface temperatures at the particular surroundings in which he finds himself after equilibrium has been reached with no clothing covering those surfaces.

The equipment that can be employed as thermographic equipment is known to the art. The equipment employed to make thermographic examinations for breast cancer, for example, may be employed. It is preferred that the equipment employed be equipment sensitive to infrared radiations and which displays surfaces having different temperatures as surfaces having different colors and generally displays on a cathode ray tube much like a color television tube a recognizable portion of the body being scanned as far as overall outlines are concerned.

One suitable piece of equipment for this purpose is the Thermovision system which is a product of AGA Corporation. As stated hereinabove, the scan may be general or over a specific area. But in either event the scan is conducted to locate a temperature aberration.

A temperature aberration is defined as an observable temperature that is not consistent with the general temperature norm of the subject. The most frequent temperature aberrations are asymmetrical temperature aberrations. For example, one shoulder may be significantly hotter than the other. Another temperature aberration may be an isolated area that is at a temperature unexpected for that area. An example of such a temperature aberration would be a band around a subject's chest that is at a significantly different temperature than adjacent areas, or that is in such a pattern as to suggest a psychophysiological condition.

Still another temperature aberration is an area at a temperature that is inconsistent with what is known for temperatures of that area: for example, a subject's eyes that are at a significantly different temperature than the eyes of almost any other subject — in other words, simply an abnormal temperature.

When an area having a temperature aberration has been found, the subject is placed in an hypnotic state. The hypnotic state is induced by conventional methods which are now well known, very predictable, and widely used in medicine, dentistry, and particularly in psychiatry.

In an hypnotic state, people are capable of intense focus of attention on a particular area of the body. Subjects in an hypnotic state are also capable of being regressed to an earlier period of their lives. The regression has the effect of the subject reexperiencing a chronologically earlier experience. When the subject has his attention focused on a particular part of his body and is regressed, a traumatic experience that was significant to that part of the body under focus will be reexperienced in such manner that it will be brought into the subject's conscious awareness when he is no longer in the hypnotic state.

When the subject is regressed to the point where he is reexperiencing the traumatic experience that is the basis for his physiologic condition, the temperature aberration visible on the display becomes unstable. For example, if the temperature aberration is an uncharacteristically cool area resulting from restricted blood flow caused by a tense muscle, that aberration becomes unstable by quickly becoming significantly warmer. Frequently the instability is manifested to the extent of causing a different temperature aberration — for example, the uncharacteristically cool area may temporarily become uncharacteristically warm. Any instability of the aberration indicates progress in the treatment of the condition, and the therapist observing the visual display can observe an objective indication of the progress of the treatment. Typically, when the temperature aberration becomes unstable, it becomes highly unstable and changes rapidly and significantly, after which the temperature of the subject restabilizes but in a condition where there is no temperature aberration, or at least where there is a significantly lesser temperature aberration than was originally observed.

In a preferred embodiment of this invention, the subject while under hypnosis observes the visual display. It has been found very effective to have the subject observe the display during this period because the coincidence of his changing feelings and of the changing pattern of the temperature aberration provides a feedback to the subject that aids in effecting the process of change. In effect, the subject obtains direct communication from his own cellular makeup as to the progress of his treatment, and this feedback apparently provides the subject some control over the progress of the process. A therapist can, of course, observe the process via a display but is less capable of participating than is the subject.

When the temperature aberration has been unstable to a sufficient extent or when the subject's temperature restabilizes without a temperature aberration, the subject is brought out of the hypnotic state. Generally, the subject has awareness of what happened during the hypnotic state and regression, and he has a very acute memory of the traumatizing experience that was the basis for the psychophysiologic condition. The subject after one treatment usually has a great understanding of the condition and either complete or a significant degree of relief from it. The relief produced from the treatment apparently is permanent.

DETAILED DESCRIPTION OF THE INVENTION

A young male adult suffered chronically from extreme tension in his shoulder muscles that was particularly prevalent in periods of emotional stress and caused discomfort and headaches. A temperature scan of the chest and shoulders of the subject's body was made, and it was found that a temperature aberration existed in that the subject's shoulder areas were cooler than adjacent areas to an uncharacteristic degree. The subject was placed in an hypnotic state; his attention was focused on his shoulders; and he was regressed. When in a very deep trance, the subject quickly arrived at a memory of an experience he had at the age of seven years. The experience was that he and an older brother while at a playground became involved in a fight with two other boys. One of the boys had grabbed the subject around the neck and began strangling him. In the hypnotic trance the subject became distraught by the tightness around his neck and was acting as though he was literally being choked even though nothing was touching his neck.

The therapist told the subject to do whatever he had to do to make the choking go away, and the subject cried out for his brother to help him, just as he had done when he was seven. The subject was then brought out of the hypnotic condition, and the thermographic image was entirely different from the one that had existed previously. During and immediately after regression, a highly unstable thermographic image was produced which included several aberrations such as extremely high temperature in the subject's eyes, but the temperature profile eventually stabilized to a normal profile that was the same as the subject's previous temperature profile except that the coolness around the shoulders was gone. The tenseness of the muscles that the subject previously experienced was also gone, and the relief of the condition apparently is permanent.

The entire procedure described above was accomplished in 45 minutes. The locus of the memory of the traumatic experience was quickly isolated by the objective temperature scan, and the experience that was the psychological basis for the trauma was quickly revealed by the combination of hypnosis, focusing attention on the shoulders, and regression. Although similar to psychoanalytic processes, the process described above quickly located the site and the cause of the psychophysiologic condition and rapidly brought it into the subject's conscious awareness.

What is claimed is:
1. The process for treating a psychophysiologic condition comprising

A. scanning a human subject with a thermographic means having a visual display of temperature variations over the body of said subject,
B. determining areas having temperature aberrations,
C. inducing an hypnotic state in said subject,
D. focusing the attention of said subject while in said state on the area displaying a temperature aberration and regressing said subject to a traumatizing experience affecting said area,
E. maintaining said subject's attention focused on said traumatizing experience until said temperature aberration becomes unstable, and
F. bringing said subject out of said hypnotic state.

2. The process of claim 1 wherein said subject observes said visual display during regression.

3. The process of claim 1 wherein a restricted area of the subject's body is scanned.

* * * * *